US007851511B2

(12) United States Patent
Allef et al.

(10) Patent No.: US 7,851,511 B2
(45) Date of Patent: Dec. 14, 2010

(54) EMULSIFIER FOR HIGHLY LIQUID W/O EMULSION BASED ON PARTLY CROSSLINKED POLYGLYCEROL ESTERS OF POLYHYDROXYSTEARIC ACID

(75) Inventors: Petra Allef, Essen (DE); Wolfgang Berkels, Bottrop (DE); Thomas Dietz, Glen Allen, VA (US); Burghard Grüning, Essen (DE); Peter Hameyer, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 1081 days.

(21) Appl. No.: 10/896,815

(22) Filed: Jul. 22, 2004

(65) Prior Publication Data

US 2005/0031580 A1 Feb. 10, 2005

(30) Foreign Application Priority Data

Jul. 23, 2003 (DE) ................................ 103 33 443

(51) Int. Cl.
*A01N 25/00* (2006.01)
*A61K 47/00* (2006.01)
*A61K 8/02* (2006.01)
*C07C 51/00* (2006.01)
*C11C 1/00* (2006.01)
*C11C 3/00* (2006.01)

(52) U.S. Cl. ....................... 514/785; 514/772; 514/844; 514/937; 424/401; 554/166

(58) Field of Classification Search ................. 514/785, 514/937, 772, 844; 424/401; 554/166
See application file for complete search history.

(56) References Cited

U.S. PATENT DOCUMENTS 5,840,943 A * 11/1998 Ansmann et al. ............ 554/166
6,242,499 B1 * 6/2001 Gruning et al. ............. 514/785

FOREIGN PATENT DOCUMENTS

| | | | |
|---|---|---|---|
| DE | 4012693 | A1 | 10/1991 |
| DE | 4409569 | C1 | 8/1995 |
| DE | 4420516 | A1 | 12/1995 |
| EP | 0904773 | A2 | 3/1999 |
| EP | 0835862 | B1 | 3/2001 |

OTHER PUBLICATIONS

European Search Report dated Jul. 22, 2010.

* cited by examiner

*Primary Examiner*—Sreeni Padmanabhan
*Assistant Examiner*—Samira Jean-Louis
(74) *Attorney, Agent, or Firm*—Scully, Scott, Murphy & Presser, P.C.

(57) ABSTRACT

The present invention relates to polyglycerol partial esters of polyhydroxystearic acid and polyfunctional carboxylic acids which are obtainable by esterification of a polyglycerol mixture with polyhydroxystearic acid where N=1 to 10, preferably 2 to 8, in particular 3 to 5 units and dimer fatty acids which have been obtained by catalytic dimerization of unsaturated fatty acids having 12 to 22 C atoms and have an average functionality of 2 to 3, and/or with aliphatic, linear or branched dicarboxylic acids having a chain length of 2 to 16 C atoms and additionally saturated or unsaturated, linear or branched fatty acids having 6 to 22 C atoms, preferably 12 to 18 C atoms, the degree of esterification of the polyglycerol mixture being between 20 and 75%, preferably 40 to 70%.

12 Claims, No Drawings

EMULSIFIER FOR HIGHLY LIQUID W/O EMULSION BASED ON PARTLY CROSSLINKED POLYGLYCEROL ESTERS OF POLYHYDROXYSTEARIC ACID

FIELD OF THE INVENTION

The present invention relates to polyglycerol partial esters of polyhydroxystearic acid and polyfunctional carboxylic acids which are obtainable by esterification of a polyglycerol mixture with polyhydroxystearic acid where N=1 to 10 units and either dimer fatty acids which have been obtained by catalytic dimerization of unsaturated fatty acids having 12 to 22 C atoms and have an average functionality of 2 to 3, or with aliphatic, linear or branched dicarboxylic acids having a chain length of 2 to 16 C atoms and additionally saturated or unsaturated, linear or branched fatty acids having 6 to 22 C atoms, the degree of esterification of the polyglycerol mixture being between 20 and 75%. The present invention also relates to the preparation thereof and their use as W/O emulsifiers in cosmetic or pharmaceutical formulations and as auxiliaries for dispersing inorganic micropigments in oily dispersions.

BACKGROUND OF THE INVENTION

It is known to one skilled in the art that water-in-oil emulsions are difficult to stabilize against coalescence of the water droplets and therefore against the separating out of water. The reason behind this is due to the dense packing of the water droplets, as a consequence of the usually high content of disperse phase (>65%). A further consequence of the high packing density is a high viscosity per se of the emulsion. To achieve an adequate stability required by the cosmetic's industry, stabilizing waxes and, in some cases, high-viscosity oils, both of which increase the viscosity of the (external) oily phase, and thus reduce the mobility of the water droplets and protect against coalescence, are used. However, high-viscosity oils and stabilizing waxes have an adverse influence on the sensation on the skin, which manifests itself in a heavy and tacky feeling. Oil-in-water emulsions, which are known to have a lighter sensation on the skin, can in principle be used as an alternative, but water-in-oil emulsions have a significantly better care effect than oil-in-water emulsions.

A generally worthwhile aim is thus to make water-in-oil emulsions as light as possible, i.e., as low-viscosity as oil-in-water emulsions, without having to surrender their particular care effect. Furthermore, there is a need to make water-in-oil emulsions that are not tacky, yet are stable. The emulsifier to be used plays a particular key role in this context.

For ecological reasons, there is a considerable interest, both among producers and among consumers of emulsion preparations, in W/O emulsifiers which are based on natural raw materials. Partial esters of polyalcohols, such as glycerol, polyglycerol, sorbitol or methyl glycoside, and fatty acids, such as oleic or isostearic acid, find diverse uses for this reason.

However, this type of emulsifier is not suitable for stabilizng flowable emulsions (lotions) and creams with a high content of natural triglycerides. In addition to the W/O emulsifiers mentioned, the creams which meet the stability requirements of the market (resistance to temperatures from −15 to +45° C., in some cases from −25 to +50° C. comprise as lipid-like components predominantly paraffin oils and fatty acid ester of monoalkanols (MW<500); these have more favorable technological properties than the higher molecular weight triglycerides. Nevertheless, relatively high concentrations of viscosity-increasing waxes (≧3%) are required for the stabilization, these having an adverse effect on the application properties since they produce an undesirable tacky-greasy feeling on the skins.

Coemulsifiers, in particular ethylene oxide adducts in combination with metal soaps, extend the field of use only to lotions comprising paraffin oil.

The polyglycerol esters of dimeric and polymerized unsaturated $C_{18}$-fatty acids have considerably better emulsifying properties than the polyalcohol fatty acid partial esters. They are obtained from the mono- and diglycerides of plant oils, preferably soya oil, by a heat treatment at approximately 300° C. for several hours or by transesterification of a thermally polymerized plant oil with polyglycerol.

The polyglycerol polyricinoleates formed from castor oil by an analogous process are also efficient W/O emulsifiers. This is described, for example, in DE-B44 09 569.

Both classes of substances have not been able to establish themselves in cosmetic or pharmaceutical emulsion preparations because of their sensitivity to oxidation and the often greasy-rancid smell. The massive exposure to heat during the preparation and the unsaturated character (iodine number approximately 100) are primarily responsible for this.

In contrast polyglycerol polyhydroxystearate, which is related chemically to polyglycerol polyricinoleate and can also be prepared from vegetable raw materials, has a satisfactory sensorial quality and has the main capability of forming cream-like and, in particular, flowable W/O emulsions.

DE-A40 12 693 has proposed esters of polycarboxylic acids with polyhydroxy compounds. Condensation of the starting compounds gives products with excess carboxyl groups, which are then neutralized. The reaction products are suitable as O/W emulsifiers.

EP-B-0 835 862 describes polyglyerol partial esters which are obtainable by esterification of a polyglycerol mixture having a degree of esterification of the polyglycerol of between 30 and 75% and saturated or unsaturated, linear or branched fatty acids having 12 to 22 C atoms and dimer fatty acids having an average functionality of 2 to 2.4. These have the additional advantage over polyglycerol polyhydroxystearate of an improved stability, in particular a higher resistance to freezing-thawing of the W/O emulsions prepared with them. However, the emulsions are still relatively viscous and cause a slightly tacky sensation on the skin.

The improvement in the resistance to freezing-thawing is of considerable practical interest for the transportability and storability of the emulsion preparations. By relatively long storage at very low temperatures or by extreme variations in temperature over relatively long transportation routes, the inadequate emulsion stabilization can manifest itself by significant separating out of water in the emulsion preparation or can even lead to complete breaking of the emulsion.

SUMMARY OF THE INVENTION

An object of the present invention is to develop an emulsifier that allows formulation of highly liquid emulsions which have a pleasant sensation on the skin and at the same time an improved resistance to freezing-thawing.

It has now been found, surprisingly, that in particular low-viscosity, but at the same time, particularly stable, water-in-oil emulsions can be obtained if polyglycerol partial esters of polyhydroxystearic acid, which are additionally linked with dicarboxylic acids, are used as emulsifiers.

The present invention therefore relates to polyglycerol partial esters of polyhydroxystearic acid and polyfunctional carboxylic acids which are obtainable by esterification of a polyglycerol mixture with polyhydroxystearic acid where N=1 to 10, preferably 2 to 8, in particular 2 to 5 units and dimer fatty acids which have been obtained by catalytic dimerization of unsaturated fatty acids having 12 to 22 C atoms and have an average functionality of 2 to 3, and/or with aliphatic, linear or branched di- and/or tricarboxylic acids having a chain length of 2 to 16 C atoms and additionally saturated or unsaturated, linear or branched fatty acids having 6 to 22 C atoms, preferably 12 to 18 C atoms, the degree of esterification of the polyglycerol mixture being between 20 and 75%, preferably 40 to 70%.

The present invention further relates to the use of the inventive polyglycerol partial esters as W/O emulsifiers in cosmetic or pharmaceutical formulations.

It has been found, surprisingly, that strongly polar plant oils can also be incorporated into stable emulsions, while with these products conventional emulsifiers lead to emulsifiers that are unstable at low temperatures. The condensation products based on 12-hydroxystearic acid are liquid and are also suitable for energy-saving “cold-cold” preparation of emulsions, in addition to the conventional “hot-hot” preparation.

DETAILED DESCRIPTION OF THE INVENTION

The present invention, which provides emulsifiers that are based on partly crosslinked polyglycerol esters of polyhydroxystearic acid, will now be described in greater detail. The polyhydroxystearic acids co-used according to the present invention are prepared, for example, by polycondensation of hydroxystearic acid, preferably 12-hydroxystearic acid, which is obtained by hardening of ricinoleic acid or technical-grade castor oil fatty acid, by known processes. Esterification products of the following general formula are obtained:

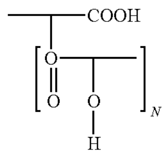

where

N=1 to 10, preferably 2 to 8, in particular 2 to 5 fatty acid units, are formed, these having acid numbers of between 187 and 20, preferably between 96 and 45.

Suitable polyglycerols are, in particular, those of the general formula

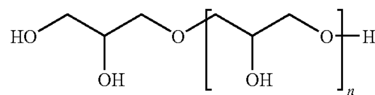

having an average degree of condensation n of 1 to 11, preferably 2 to 6, particularly preferably 3 to 6, and hydroxyl numbers of approximately 1,350 to approximately 800, preferably approximately 1,200 to approximately 900.

These are technical-grade polyglycerol mixtures which are obtained, e.g., by alkali-catalysed condensation of glycerol at elevated temperatures, and from which fractions having the desired degree of condensation can optionally be obtained by distillation processes. Polyglycerols, which are obtained by another route, e.g., from epichlorohydrin or glycidol, are also suitable.

The use of polyglycerols which have the following distribution of homologues (GC method) has proved to be particularly advantageous; the preferred ranges are stated in parentheses:

Glycerol: 0 to 20 (<5) wt. %
Diglycerols: 0 to 60 (5 to 30) wt. %
Triglycerols: 0 to 60 (5 to 50) wt. %
Tetraglycerols: 0 to 30 (5 to 25) wt. %
Pentaglycerols: 0 to 30 (5 to 20) wt. %
Oligoglycerols: to 100 wt. %

As is known, the dimer fatty acids employed are a mix of acyclic and cyclic dicarboxylic acids which are obtained by a catalysed dimerization of unsaturated fatty acids having 12 to 22 C atoms and have an average functionality of 2 to 3, preferably approximately 2. They can also comprise polymeric fatty acids (trimeric and of higher functionality) in a minor amount. The acid numbers are in the range from 150 to 290, preferably 190 to 200.

Commercially available products have on average

| | |
|---|---|
| monomer contents of approximately | 7 to 15 wt. % |
| dimer contents of approximately | 70 to 77 wt. % |
| polymer contents of approximately | 15 to 16 wt. %. |

They can be adjusted to higher contents of the particular functionalities (mono, di, tri) by known separation processes and/or to low contents of unsaturated fatty acids (low iodine numbers) by hydrogenation Further information is to be found in the products sheets of the manufacturers, such as, for example, of Uniqema (Pripol®) and Arizona Chem. (Unidyme®, Century®).

For the preparation and use of dimer acids and the physical and chemical properties thereof, reference is also made to the publication “The Dimer Acids: The chemical and physical properties, reactions and applications”, ed. E. C. Leonard; Humko Sheffield Chemical, 1975, Memphis, Tenn. The content of the aforementioned reference is incorporated herein by reference.

The use of relatively short-chain di- or tricarboxylic acids instead of dimer acids, such as oxalic acid, malonic acid, succinic acid, glutaric acid, adipic acid, pimelic acid, suberic acid, azelaic acid, sebacic acid and dodecandioic acid, is particularly suitable for the intended use according to the invention as emulsifiers. Hydroxydi- and -tricarboxylic acids, such as malic acid, tartaric acid and citric acid, are also suitable.

The alkanedicarboxylic acids having 4 to 14 C atoms are particularly preferred.

A significantly improved stabilization of the phase boundaries in W/O emulsions can be achieved by the co-use of these acids.

Suitable additional fatty acid components are, above all, saturated fatty acids, such as lauric acid, tridecanoic acid, myristic acid, palmitic acid, margaric acid, stearic acid, isostearic acid, arachic acid and behenic acid as well as mixtures thereof.

Naturally occurring mixtures are, for example, the coconut fatty acids, which comprise as the main constituent lauric acid, and, in addition, saturated $C_{14}$- to $C_{18}$-fatty acids and optionally saturated $C_8$- to $C_{10}$-fatty acids and unsaturated fatty acids, as well as tallow fatty acids, which are substantially a mixture of palmitic acid and stearic acid.

Suitable additional unsaturated fatty acid components are mono-olefinically unsaturated acids, for example hexadecenoic acids, octadecenoic acids, such as oleic acid (cis-9- octadecenoic acid) or elaidic acid (trans-9-octadecenoic acid), eicosenoic acids and docosenoic acids, such as erucic acid (cis-13-docosenoic acid) or brassidic acid (trans-13-docosenoic acid), polyunsaturated fatty acids, for example octadecadienoic acids and octadecatrienoic acids, such as linoleic acid and linolenic acid, and mixtures thereof.

The liquid fatty acids, such as oleic, ricinoleic, erucic and isostearic acid, which contain 18 to 22 carbon atoms are particularly suitable. Their solidification points are below 35° C. because of a branching or a double bond in the hydrocarbon chain. Fatty acid mixtures, which can also comprise waxy components, such as hardened ricinoleic acid, can furthermore be used. The use of lactones, such as butyrolactone or caprolactone, as the fatty acid component is also possible.

In the polyglycerol partial esters according to the present invention, the hydroxyl groups of the polyglycerol are esterified to the extent of 20 to 75%, preferably 40 to 70%.

For their preparation, variants A) and B) described below are preferred:

A) in a first stage polyglycerol is esterified with fatty acid and dicarboxylic acid and/or dimer acid up to a degree of esterification of 10 to 70%, preferably 25 to 40%, and in a second stage the product is esterified with polyhydroxystearic acid to a total degree of esterification of 20 to 75%, preferably 40 to 60%, or in a B) first stage polyglycerol is esterified with fatty acid and polyhydroxystearic acid up to a degree of esterification of 10 to 70%, preferably 25 to 40%, and in a second stage the product is esterified with dicarboxylic acid and/or dimer acid to a total degree of esterification of 20 to 75%, preferably 40 to 60%.

Other sequences of addition of the fatty acids and one-pot processes are also possible.

The molar ratio according to the present invention of polyhydroxystearic acid to di-acid/dimer acid to fatty acid is in the range of 0.25 to 4 mol: 0.1 to 2 mol: 0 to 10 mol, preferably in the range of 0.25 to 2 mol: 0.3 to 1 mol: 0.5 to 3 mol an HLB value of approximately 3 to 8 being established by suitable choice of the hydrophilic and lipophilic molecular contents in order to obtain favorable properties for the stabilization of W/O emulsions. This is achieved in that the content of hydrophilic components is in the range of 10 to 70%, preferably 20 to 40%.

The polyglycerol partial esters according to the present invention can be prepared in a manner known per se by heating the reaction components and separating off the resulting water of reaction by distillation. Acidic or basic catalysts, such as sulfonic acids, phosphoric acid or phosphorous acid, Lewis acids, such as tin salts, or alkali metal or alkaline earth metal oxides or hydroxides, alcoholates or salts, can be co-used to accelerate the reaction However, the addition of a catalyst is not absolutely necessary. The progressive conversion can be monitored, for example, via the water of reaction separated off, by measurement of the acid number or by infrared spectroscopy. In general, an acid number in the end product of <20, preferably <10 is aimed for. Products having an acid number of <5 are particularly preferred.

The polyglycerol esters according to the present invention are suitable for stabilization of aqueous emulsions and dispersions.

Their use as emulsifiers for the preparation of cosmetic or pharmaceutical formulations is preferred Possible cosmetic formulations are those which acquire an easily spreadable consistency by using oil-in-water or water-in-oil emulsifiers, because by means of these emulsifier systems an oil or a fit can be readily incorporated into an aqueous phase or an aqueous phase can be readily incorporated into an oil or a fit, for example creams, such as care creams, baby creams or sun protection creams, ointments, lotions or make-up. In pharmaceutical formulations, such as ointments or creams, oil-in-water or water-in-oil emulsifiers are required for application of active compounds.

Oil components which can be employed are:

- ester oils, such as octyl palmitate, octyl stearate, cetyl octanoate, caprylic/capric acid triglycerides, decyl oleate, cetearyl octanoate, isopropyl myristate, isopropyl palmitate, $C_{12-13}$-alkyl benzoate, stearyl heptanoate, dibutyl adipates
- plant oils, such as wheat germ oil jojoba oil, olive oil, borage oil, avocado oil, groundnut oil, almond oil, sunflower oil, walnut oil
- higher alcohols, such as octyldodecanol (or guerbet alcohols generally), oleyl alcohol, and
- paraffinic (hydrocarbon) oils, such as paraffin oil, isohexadecanes, polydecenes, Vaseline, paraffinum perliquidum, squalane.

The conventional compositions and constituents as well as conventional auxiliaries known to one skilled in cosmetic and pharmaceutical uses, such as stabilizes or preservatives, are also used for such cosmetic and pharmaceutical formulations.

The polyglyerol partial esters used according to the present invention have the effect, compared with the prior ark of a significantly increased low-temperature storage stability of the cosmetic and pharmaceutical formulations prepared with them, which is of particular importance in the case of water-in-oil emulsions, which are more difficult to stabilize compared with oil-in-water emulsions.

As a rule, lower concentrations of the polyglycerol partial esters and/or lower amounts of consistency-imparting waxes are required in the formulations in order to achieve the same action as with agents of the prior art. The water-in-oil emulsions prepared with the polyglycerol partial esters according to the present invention are more highly liquid than similarly stable emulsions pied with emulsifiers of the prior art.

The following examples are provided to illustrate the synthesis used in the present invention in making the partly crosslinked polyglycerol esters of polyhydroxystearic acid as well as their use as an emulsifier for highly liquid W/O emulsions.

Example 1

In the first stage, polyglycerol (hydroxyl number (OHN)=1,090) was esterified with fatty acid 88.4 g (0.31 mol) of isostearic acid and 157.5 g (0.13 mol) of polyhydroxystearic acid having an acid number (AN) of 47 were esterified with 100 g of polyglycerol in the first stage at 240° C. and while passing nitrogen through. After a reaction time of 2 hours at this temperature, the acid number was <10. In the second stage, the mixture was cooled to 130° C. and 22.5 g (0.11 mol) of sebacic acid were added The mixture was heated again to 240° C. and stirred at this temperature for 3 hours. A viscous product having an acid number of <5 was obtained

Example 2

91.1 g (0.32 mol) of isostearic acid and 141.7 g (0.12 mol) of polyhydroxystearic acid having an acid number (AN) of 47 were esterified with 61.9 g of polyglycerol (OHN=950) at 240° C. and while passing nitrogen through After a reaction time of 2 hours at this temperature, the acid number was <10. In the second stage, the mixture was cooled to 130° C. and 20.2 g (0.1 mol) of sebacic acid were added. The mixture was heated again to 240° C. and stirred at this temperature for 3 hours. A viscous product having an acid number of <5 was obtained Example 3

120.0 g (0.42 mol) of isostearic acid and 75.0 g (0.17 mol) of polyhydroxystearic acid having an acid number (AN) of 47 were esterified with 75.0 g of polyglycerol (OHN=950) at 240° C. and while passing nitrogen through. After a reaction time of 2 hours at this temperature, the acid number was <10. In the second stage, the mixture was cooled to 130° C. and 20.2 g (0.1 mol) of sebacic acid were added The mixture was heated again to 240° C. and stirred at this temperature for 3 hours. A viscous product having an acid number of <5 was obtained Example 4

111.8 g (0.39 mol) of isostearic acid and 110.4 g (0.09 mol) of polyhydroxystearic acid having an acid number (AN) of 47 were esterified with 61.9 g of polyglycerol (OHN=1,090) at 240° C. and while passing nitrogen through. After a reaction time of 2 hours at this temperature, the acid number was <10. In the second stage, the mix was cooled to 130° C. and 20.2 g (0.1 mol) of sebacic acid were added The mixture was heated again to 240° C. and stirred at this temperature for 3 hours. A viscous product having an acid number of <5 was obtained Example 5

91.1 g (0.32 mol) of isostearic acid and 141.7 g (0.12 mol) of polyhydroxystearic acid having an acid number (AN) of 45 were esterified with 61.9 g of polyglycerol (OHN=1,090) in the first stage at 240° C. and while passing nitrogen through After a reaction time of 2 hours at this temperature, the acid number was <10. The mixture was then cooled to 180° C. and 57.5 g (0.1 mol) of dimer fatty acid (Empol 1.062) are added The mixture was heated again to 240° C. and stirred at this temperature for 3 hours. A viscous product which was characterized by an acid number of <5 was obtained Example 6

91.1 g (0.32 mol) of isostearic acid and 141.7 g (0.12 mol) of polyhydroxystearic acid having an acid number (AN) of 45 were esterified with 61.9 g of polyglycerol (OHN=1,090) in the first stage at 240° C. and while passing nitrogen through. After a reaction time of 2 hours at this temperature, the acid number was <10. The mixture was then cooled to 130° C. and 14.6 g (0.1 mol) of adipic acid were added. The mixture was heated again to 240° C. and stirred at this temperature for 3 hours. A viscous product which was characterized by an acid number of <5 was obtained.

Example 7

88.4 g (0.31 mol) of isostearic acid and 22.5 g (0.11 mol) of sebacic acid were esterified with 175.8 g of polyglycerol (OHN=850) in the first stage at 240° C. while passing nitrogen through. After a reaction time of 2 hours at this temperature, the acid number was <10. 157.5 g (0.13 mol) of polyhydroxystearic acid having an acid number (AN) of 45 were then added at 240° C. while passing nitrogen through. The mixture was then stirred at 240° C. until the AN was <5.

Example 8

91.1 g (0.32 mol) of isostearic acid and 20.2 g (0.1 mol) of sebacic acid were esterified with 61.9 g of polyglycerol (OHN=1,090) in the first stage at 240° C. while passing nitrogen through. After a reaction time of 2 hours at this temperature, the acid number was <10.141.7 g (0.12 mol) of polyhydroxystearic acid having an acid number (AN) of 59 were then added at 240° C. while passing nitrogen through. The mixture was then stirred at 240° C. until the AN was <5.

Example 9

215.6 g (0.2 mol) of polyhydroxystearic acid having an acid number (AN) of 48, which had been esterified beforehand with an equivalent amount of isostearic acid, were esterified in a manner known per se with 24 g of polyglycerol (OHN=1,190). After a reaction time of 2 hours at this temperature, the acid number was <10. The mixture was then cooled to 130° C. and 10.1 g (0.2 mol) of sebacic acid were added. The mixture was heated again to 240° C. and stirred at this temperature for 8 hours, until an acid number of <5 was is reached.

Example 10

The preparation of the polyglycerol ester was carried out in 1 stage. 61 g of polyglycerol (OHN=1,090), 91.1 g (0.32 mol) of isostearic acid, 20.2 g (0.1 mol) of sebacic acid and 141.7 g (0.12 mol) of polyhydroxystearic acid having an acid number (AN) of 59 were initially introduced into the reaction vessel together and the mixture was then heated up to 240° C., while passing nitrogen through, until the acid number was <5.

Example 11

91.1 g (0.32 mol) of isostearic acid, 10.1 g (0.05 mol) of sebacic acid and 6.7 g (0.05 mol) of malic acid were esterified with 61.9 g of polyglycerol (OHN=1,090) in the first stage at 240° C. while passing nitrogen through. After a reaction time of 2 hours at this temperature, the acid number was <10. 141.7 g (0.12 mol) of polyhydroxystearic acid having an acid number (AN) of 45 were then added at 240° C. while passing nitrogen through. The mixture was then stirred at 240° C. until the AN was <5.

Example 12

91.1 g (0.32 mol) of isostearic acid and 20.2 g (0.1 mol) of sebacic acid were esterified with 61.9 g of polyglycerol (OHN=850) in the first stage at 240° C. while passing nitrogen through. After a reaction time of 2 hours at this temperature, the acid number was <10.141.7 g (0.12 mol) of polyhydroxystearic acid having an acid number (AN) of 45 were then added at 240° C. while passing nitrogen through. The mixture was then stirred at 240° C. until the AN was <5.

Example 13

91.1 g (0.32 mol) of isostearic acid and 20.2 g (0.1 mol) of sebacic acid were esterified with 63 g of polyglycerol (OHN=1,190) in the first stage at 240° C. while passing nitrogen through. After a reaction time of 2 hours at this temperature, the acid number was <10.141.7 g (0.12 mol) of polyhydroxystearic acid having an acid number (AN) of 45 were then added at 240° C. while passing nitrogen through. The mixture was then stirred at 240° C. until the AN was <5.

Example 14

88.4 g (0.31 mol) of isostearic acid and 22.5 g (0.11 mol) of sebacic acid were esterified with 127.8 g of polyglycerol (OHN=890) in the first stage at 240° C. while passing nitrogen through. After a reaction time of 2 hours at this temperature, the acid number was <10.157.5 g (0.12 mol) of polyhydroxystearic acid having an acid number (AN) of 45 were then added at 240° C. while passing nitrogen through. The mixture was then stirred at 240° C. until the AN was <5.

Example 15

88.4 g (0.31 mol) of isostearic acid and 22.5 g (0.11 mol) of sebacic acid were esterified with 175.8 g of polyglycerol (OHN=850) in the first stage at 24° C. while passing nitrogen through. After a reaction time of 2 hours at this temperature, the acid number was <10. 157.5 g (0.13 mol) of polyhydroxystearic acid having an acid number (AN) of 45 were then added at 240° C. while passing nitrogen through. The mixture was then stirred at 240° C. until the AN was <5.

Example 16

132.9 g (0.47 mol) of isostearic acid and 16.9 g (0.08 mol) of sebacic acid were esterified with 51.6 g of polyglycerol (OHN=1,080) in the first stage at 240° C. while passing nitrogen through. After a reaction time of 2 hours at this temperature, the acid number was <10.237.7 g (0.2 mol) of polyhydroxystearic acid having an acid number (AN) of 45 were then added at 240° C. while passing nitrogen through. The mixture was then stirred at 240° C. until the AN was <5.

Formulation Example 1

An emulsifier from the prior art based on polyglycerol partial esters from fatty acid and dimer acid (EP-B-0 835 862) was used as the emulsifier.

| | Formulation 1A (%) | Formulation 1B (%) |
|---|---|---|
| A | | |
| Emulsifier according to the prior art | 2.50 | 2.50 |
| Castor wax | 0.25 | 0.25 |
| Ceresin W 80 | 0.25 | 0.25 |
| Paraffin oil | — | 14.00 |
| Octyl palmitate | 11.00 | 8.00 |
| $C_{8/10}$-Triglycerol | 11.00 | — |
| B | | |
| Glycerol | 3.35 | 3.35 |
| Bronopol | 0.05 | 0.05 |
| $MgSO_4 \times 7\ H_2O$ | 0.60 | 0.60 |
| Water | 71.00 | 71.00 |

Preparation:

Stir B (20° C.) into A (80° C.), homogenize, after a cooling time of 2 h repeat the homogenization.

Formulation Example 2

A different emulsifier from the prior art based on polyglycerol partial esters of polyhydroxystearic acid (DE-A-44 09 569) was used as the emulsifier.

| | Formulation 2A (%) | Formulation 2B (%) |
|---|---|---|
| A | | |
| Emulsifier according to the prior art | 2.50 | 2.50 |
| Castor wax | 0.25 | 0.25 |
| Ceresin W 80 | 0.25 | 0.25 |
| Paraffin oil | — | 14.00 |
| Octyl palmitate | 11.00 | 8.00 |
| $C_{8/10}$-Triglycerol | 11.00 | — |
| B | | |
| Glycerol | 3.35 | 3.35 |
| Bronopol | 0.05 | 0.05 |
| $MgSO_4 \times 7\ H_2O$ | 0.60 | 0.60 |
| Water | 71.00 | 71.00 |

Preparation:

Stir B (20° C.) into A (80° C.), homogenize, after a cooling time of 2 h repeat the homogenization.

Formulation Example 3

An emulsifier according to embodiment example 1 was used as the emulsifier.

| | Formulation 3A (%) | Formulation 3B (%) |
|---|---|---|
| A | | |
| Emulsifier according to embodiment ex. 1 | 2.50 | 2.50 |
| Castor wax | 0.25 | 0.25 |
| Ceresin W 80 | 0.25 | 0.25 |
| Paraffin oil | — | 14.00 |
| Octyl palmitate | 11.00 | 8.00 |
| $C_{8/10}$-Triglycerol | 11.00 | — |
| B | | |
| Glycerol | 3.35 | 3.35 |
| Bronopol | 0.05 | 0.05 |
| $MgSO_4 \times 7\ H_2O$ | 0.60 | 0.60 |
| Water | 71.00 | 71.00 |

Preparation:

Stir B (20° C.) into A (80° C.), homogenize, after a cooling time of 2 h repeat the homogenization.

Formulation Example 4

An emulsifier according to embodiment example 2 was used as the emulsifier.

| | Formulation 4A (%) | Formulation 4B (%) |
|---|---|---|
| A | | |
| Emulsifier according to embodiment ex. 2 | 2.50 | 2.50 |
| Castor wax | 0.25 | 0.25 |
| Ceresin W 80 | 0.25 | 0.25 |
| Paraffin oil | — | 14.00 |
| Octyl palmitate | 11.00 | 8.00 |
| $C_{8/10}$-Triglycerol | 11.00 | — |

-continued

| | Formulation 4A (%) | Formulation 4B (%) |
|---|---|---|
| B | | |
| Glycerol | 3.35 | 3.35 |
| Bronopol | 0.05 | 0.05 |
| $MgSO_4 \times 7\,H_2O$ | 0.60 | 0.60 |
| Water | 71.00 | 71.00 |

Preparation:

Stir B (20° C.) into A (80° C.), homogenize, after a cooling time of 2 h repeat the homogenization.

Formulation Example 5

An emulsifier according to embodiment example 3 was used as the emulsifier.

| | Formulation 5A % | Formulation 5B % |
|---|---|---|
| A | | |
| Emulsifier according to embodiment ex. 3 | 2.50 | 2.50 |
| Castor wax | 0.25 | 0.25 |
| Ceresin W 80 | 0.25 | 0.25 |
| Paraffin oil | — | 14.00 |
| Octyl palmitate | 11.00 | 8.00 |
| $C_{8/10}$-Triglycerol | 11.00 | — |
| B | | |
| Glycerol | 3.35 | 3.35 |
| Bronopol | 0.05 | 0.05 |
| $MgSO_4 \times 7\,H_2O$ | 0.60 | 0.60 |
| Water | 71.00 | 71.00 |

Preparation: p Stir B (20° C.) into A (80° C.), homogenize, after a cooling time of 2 h repeat the homogenization.

Formulation Example 6

An emulsifier according to embodiment example 4 was used as the emulsifier.

| | Formulation 6A (%) | Formulation 6B (%) |
|---|---|---|
| A | | |
| Emulsifier according to embodiment ex. 4 | 2.50 | 2.50 |
| Castor wax | 0.25 | 0.25 |
| Ceresin W 80 | 0.25 | 0.25 |
| Paraffin oil | — | 14.00 |
| Octyl palmitate | 11.00 | 8.00 |
| $C_{8/10}$-Triglycerol | 11.00 | — |
| B | | |
| Glycerol | 3.35 | 3.35 |
| Bronopol | 0.05 | 0.05 |
| $MgSO_4 \times 7\,H_2O$ | 0.60 | 0.60 |
| Water | 71.00 | 71.00 |

Preparation:

Stir B (20° C.) into A (80° C.), homogenize, after a cooling time of 2 h repeat the homogenization.

While emulsions 3A, 3B, 4A, 4B, 5A, 5B, 6A and 6B, prepared with an emulsifier according to the invention, had a low viscosity (Brookfield RVT Helipath Stand, model D; V.A.C. 230, spindle C), emulsion 1A and 1B, prepared with an emulsifier from the prior art based on polyglycerol partial esters from fatty acid and dimer acid (EP-B-0 835 862), had an increased viscosity and therefore a slightly tacky sensation on the skin.

Emulsions 2A and 2B, prepared with an emulsifier from the prior art based on polyglycerol partial esters of polyhydroxystearic acid (DE 44 20 516), showed a moderate viscosity, but a significant separating out of water after storage at low temperatures (12 h at −15° C. or −25 C), which made transportation of the emulsions difficult.

The results are summarized in the following table:

| | Viscosity [Pas] | Stability |
|---|---|---|
| Emulsion 1A | 28 | stable |
| Emulsion 1B | 23 | stable |
| Emulsion 2A | 19 | separating out of water at −15° C. |
| Emulsion 2B | 15 | separating out of water at −25° C. |
| Emulsion 3A | 13 | stable |
| Emulsion 3B | 8 | stable |
| Emulsion 4A | 13 | stable |
| Emulsion 4B | 10 | stable |
| Emulsion 5A | 12 | stable |
| Emulsion 5B | 10 | stable |
| Emulsion 6A | 11 | stable |
| Emulsion 6B | 9 | stable |

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What we claim is:

1. A W/O emulsifier for cosmetic or pharmaceutical formulations comprising at least a polyglycerol partial ester of polyhydroxystearic acid and polyfunctional carboxylic acids, obtainable by esterification of a a) polyglycerol mixture, with b) polyhydroxystearic acid and c) di-, tricarboxylic acids or mixtures thereof, wherein said emulsifier provides a W/O emulsion having a viscosity of 13 Pas or less that is stable when cooled to −15° C. or below.

2. A W/O emulsifier as claimed in claim 1, wherein the polyglycerol mixture has an average degree of condensation of 1 to 10.

3. A W/O emulsifier as claimed in claim 1, wherein the polyhydroxystearic acid has an average degree of condensation of 1 to 10.

4. A W/O emulsifier as claimed in claim 1, wherein component c) comprises aliphatic, linear or branched dicarboxylic acids that contain 2 to 16 C atoms.

5. A W/O emulsifier as claimed in claim 1, wherein the polyglycerol partial ester further comprising at least one dimer fatty acid.

6. A W/O emulsifier as claimed in claim 5, wherein the at least one dimer fatty acid has an average functionality of 2 to 3.

7. A W/O emulsifier as claimed in claim 1, wherein the polyglycerol partial ester further comprising at least one fatty acid having 6 to 22 carbon atoms.

8. A W/O emulsifier as claimed in claim 1, wherein the polyglycerol partial ester further comprising at least one dimer fatty acid and at least one fatty acid having 6 to 22 carbon atoms.

9. A W/O emulsifier as claimed in claim 7, wherein the at least one fatty acid comprises a saturated or unsaturated, linear or branched monobasic acid having 6 to 22 C atoms.

10. A W/O emulsifier as claimed in claim 1, wherein the degree of esterification of the polyglycerol mixture is between 20 and 75% of the OH groups.

11. A W/O emulsifier for cosmetic or pharmaceutical formulations comprising at least a polyglycerol partial ester which is obtainable by esterification of a) 1.0 mol of OH groups of a polyglycerol mixture with b) 0.01 to 0.9 mol of COOH groups of a polyhydroxystearic acid and c) 0.01 to 0.9 mol of COOH groups of di-, tricarboxylic acids or mixtures thereof, d) 0 to 0.9 mol of COOH groups of dimer fatty acids, and e) 0.1 to 0.9 mol of COOH groups of fatty acids having 6 to 22 C atoms, with the proviso that the sum of the COOH groups approximately corresponds to 20 to 75% of the OH groups of the polyglycerol mixture, wherein said emulsifier provides a W/O emulsion having a viscosity of 13 Pas or less that is stable when stored 12 hr at −15° C. or −25° C.

12. A process for the preparation of a polyglycerol partial ester of the W/O emulsifier as claimed in claim 1 comprises, in a first stage esterification of polyglycerol with a fatty acid and di- and/or tricarboxylic acid and/or a dimer acid up to a degree of esterification of 10 to 70%, and in a second stage esterification of the product with polyhydroxystearic acid to a total degree of esterification of 20 to 75%, or in a first stage esterification of polyglycerol with a fatty acid and polyhydroxystearic acid up to a degree of esterification of 10 to 70%, and in a second stage esterification of the product with di- and/or tricarboxylic acid and/or a dimer acid to a total degree of esterification of 20 to 75%.

* * * * *